(12) United States Patent  (10) Patent No.: US 8,399,655 B2
Cimpoia et al.  (45) Date of Patent: *Mar. 19, 2013

(54) PROCESS AND METHODS FOR THE PREPARATION OF OPTICALLY ACTIVE CIS-2-HYDROXYMETHYL-4-(CYTOSIN-1'-YL)-1,3-OXATHIOLANE OR PHARMACEUTICALLY ACCEPTABLE SALTS THEREOF

(75) Inventors: Alex Cimpoia, Verdun (CA); Dan Simion, Edmonton (CA); Joana R. Simion, legal representative, Edmonton (CA)

(73) Assignee: SHIRE Canada Inc., Laval, Quebec (CA)

( * ) Notice: Subject to any disclaimer, the term of this patent is extended or adjusted under 35 U.S.C. 154(b) by 15 days.

This patent is subject to a terminal disclaimer.

(21) Appl. No.: 13/166,242

(22) Filed: Jun. 22, 2011

(65) Prior Publication Data

US 2011/0257397 A1  Oct. 20, 2011

Related U.S. Application Data

(63) Continuation of application No. 11/073,020, filed on Mar. 7, 2005, now Pat. No. 7,968,703.

(51) Int. Cl.
| | |
|---|---|
| *C07D 411/04* | (2006.01) |
| *C07D 239/47* | (2006.01) |
| *A61K 31/506* | (2006.01) |
| *A61K 31/513* | (2006.01) |
| *A61K 31/7072* | (2006.01) |
| *A61P 31/18* | (2006.01) |

(52) U.S. Cl. ...................................... 536/26.8; 544/317
(58) Field of Classification Search .................. 544/317; 536/26.8
See application file for complete search history.

(56) References Cited

U.S. PATENT DOCUMENTS

| | | | |
|---|---|---|---|
| 5,587,480 A | 12/1996 | Belleau | |
| 5,827,727 A | 10/1998 | Liotta | |
| 6,228,860 B1 | 5/2001 | Mansour | |
| 6,600,044 B2 | 7/2003 | Murthy | |
| 7,968,703 B2* | 6/2011 | Cimpoia et al. | 536/26.8 |
| 2003/0013880 A1 | 1/2003 | Murthy | |
| 2004/0214844 A1 | 10/2004 | Otto | |

FOREIGN PATENT DOCUMENTS

| | | |
|---|---|---|
| EP | 0 776 883 | 6/1997 |
| EP | 1 295 873 | 6/2001 |
| JP | 56 26848 | 3/1981 |
| JP | 01 224370 | 9/1989 |
| JP | 07 188123 | 12/1993 |
| JP | 09-208546 | 8/1997 |
| JP | 2002 080459 | 3/2002 |
| JP | 2002 193933 | 7/2002 |
| WO | WO 95/29167 | 11/1995 |

OTHER PUBLICATIONS

Japan Scientific Societies Press, Kikan Kagaku Sousetsu, No. 6, 3$^{rd}$ Edition, 45-91, 1999.
English translation of Japan Scientific Societies Press, Kikan Kagaku Sousetsu, No. 6, 3$^{rd}$ Edition, 45-91, 1999.
Patent Abstracts of Japan, Publication No. 01-224370; Date of Publication: Sep. 7, 1989. Application No. 63-047434. Date of Filing: Mar. 2, 1998. Applicant: Nippon Kayaku Co. Ltd.
Patent Abstracts of Japan, Publication No. 2002-080459; Date of Publication: Mar. 19, 2002. Application No. 2000-263694. Date of Filing: Aug. 31, 2000. Applicant: Daiwa Kasei Kogyo KK.

(Continued)

*Primary Examiner* — Venkataraman Balasubramanian
(74) *Attorney, Agent, or Firm* — Millen, White, Zelano & Branigan, P.C.

(57) ABSTRACT

There is provided a method for resolving a compound of formula III, in the cis configuration:

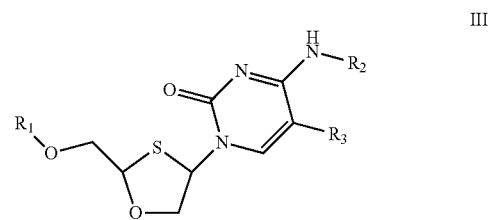

There is also provided a process for producing optically active compound of formula I or II:

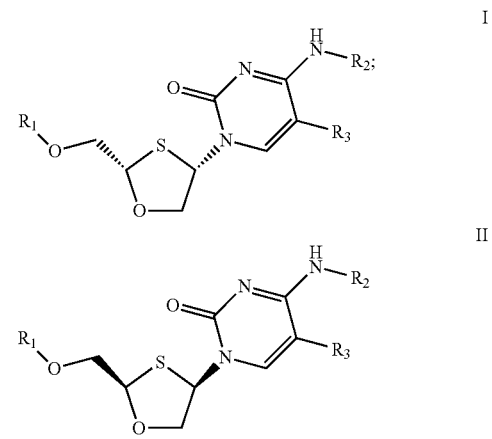

wherein: $R_1$, $R_2$, $R_3$ are as defined herein, the method and process involving the production, recovery and conversion of diastereomeric salts.

44 Claims, No Drawings

OTHER PUBLICATIONS

Patent Abstracts of Japan, Publication No. 56-026848; Date of Publication: Mar. 16, 1981. Application No. 54-102261. Date of Filing: Aug. 13, 1979. Applicant: Yamakawa Yakuhin Kogyo KK.

Patent Abstracts of Japan; Publication No. 07-188123; Date of Publication: Jul. 25, 1995. Application No. 05-331184. Date of Filing: Dec. 27, 1993. Applicant: Toray Ind Inc.

Patent Abstracts of Japan; Publication No. 09-208546; Date of Publication: Aug. 12, 1997. Application No. 07-331457. Date of Filing: Dec. 20, 1995. Applicant: Ajinomoto Co Inc.

Patent Abstracts of Japan; Publication No. 2002-193933; Date of Publication: Jul. 10, 2002. Application No. 2001-171606. Date of Filing: Jun. 6, 2001. Applicant: Toray Ind Inc.

JP-A-1-224370 English Translation of paragraph of document.

JP-A-2002-80459 English Translation of paragraph of document.

JP-A-5626848—English Translation of paragraph of document.

JP-A-7-188123—English Translation of paragraph of document.

Supplementary European Search Report of Apr. 21, 2010. European Application No. EP 05 71 4624. International Application No. PCT/CA2005/000384.

Bayley, C.R. et al.: "Resolution of Racemates by Diastereomeric Salt Formation" Chirality in Industry, Chapter 2, pp. 66-77 (1992).

Wang, W. et al. "Synthesis of Optically Active 2',3'-Dideoxy-3'-oxa-4'-thio-ribonucleoside Analogues by Transposition of a Leaving Group on Chiral Oxathiolanes via a Reductive-oxidative Process" Tetrahedron Letters, 35(27):4739-4742 (1994).

Samuel H. Wilen, "Tables of Resolving Agents and Optical Resolution", University of Notre Dame Press, 1972, pp. 24-31 and 141-195, London.

Societa Chimica Italiana, Seminars in organic synthesis, p. 172 (Jun. 2003).

\* cited by examiner

PROCESS AND METHODS FOR THE PREPARATION OF OPTICALLY ACTIVE CIS-2-HYDROXYMETHYL-4-(CYTOSIN-1'-YL)-1,3-OXATHIOLANE OR PHARMACEUTICALLY ACCEPTABLE SALTS THEREOF

This application is a continuation of U.S. patent application Ser. No. 11/073,020, filed Mar. 7, 2005 (now U.S. Pat. No. 7,968,703, issued Jun. 28, 2011).

FIELD OF INVENTION

The present invention relates to the field of making optically active compounds, particularly the preparation of optically active oxathiolane nucleosides.

BACKGROUND

Classes of compounds known as 2-substituted-4-substituted-1,3-oxathiolanes have been found to have potent antiviral activity. In particular, these compounds have been found to act as potent inhibitors of HIV-1 replication in T-lymphocytes over a prolonged period of time with less cytotoxic side effects than compounds known in the art. These compounds have also been found active against 3TC-resistant HIV strains. These compounds are also useful in prophylaxis and treatment of hepatitis B virus infections.

Cis-2-Hydroxymethyl-4-(cytosin-1'-yl)-1,3-oxathiolane can be produced by the methods described by Mansour et al., "Anti-Human Immunodeficiency Virus and Anti-Hepatitis-B Virus Activities and Toxicities of the Enantiomers of 2-Deoxy-3'-oxa-4'-thiacytidine and Their 5-Fluoro Analogues in vitro", *J. Med. Chem.*, (1995), Vol. 38, No. 1, pp. 1-4, as well as U.S. Pat. No. 6,228,860 or *Nucleosides and Nucleotides*, (1995) 14(3-5) pp. 627-735 which are incorporated herein by reference.

Typically, when compounds are desired as a single enantiomer they may be obtained either by resolution of the mixture of the two cis enantiomers by chiral HPLC or by stereospecific synthesis from isometrically pure starting material or any convenient intermediate. A complete review of known technology may be found in "Enantiomers, Racemates and Resolutions" by J. Jacques, A. Collet & S. H. When (John Wiley & Sons, 1981). Alternatively, compounds or any convenient intermediate may be resolved by enzymatic resolution with a suitable enzyme such as cytidine deaminase or selective enzymatic degradation of a suitable derivative. See for example Storer et al., "The resolution and Absolute Stereochemistry of the Enantiomers of cis-1[2(Hydroxymethyl)-1,3-Oxathiolan-5-Yl)Cytosine (BCH-189): Equipotent Anti-HIV Agents", Nucleosides & Nucleotides, 12(2), 225-236 (1993).

Another process known as resolution by formation of diastereomeric compounds require intervention of chiral agents. Unlike enantiomers, diastereomers may have significantly different physico-chemical properties that may allow for the separation from one another. One variation of such technique involves the formation and separation of diastereomeric salts between a racemic substance and an optically active resolving acid or base. Pasteur first reported the resolution of a racemic acid using an optically active base (Pasteur, L., *C.R Acad. Sci.* (1853) 37 p. 162; Pasteur, L., *Ann. Chim* (Paris) (1853) 3, 38 p. 437). A resolution using nonstochiometric quantities of chiral agents was studied by Marckwald 1896 and later referred to as "method of half-quantity" (Marckwald, W., *Ber.* (1896), 29, p. 42; Marckwald, W., *Ber.* (1896), 29, p. 43). The process for the resolution of tartaric acid through crystallization of its salt of cinchonine was improved by Marckwald while using only half of the cinchonine necessary for formation of the tartrate salt. The resolution is based on the separation of one of the diastereomers and one of the enantiomers rather than the separation of two diastereomeric salts formed in equal quantities. When using the method of half-quantity, the racemate is partially neutralized by the optically active resolving agent. In the process described by Pope & Peachey (Pope, W. J., Peachey, S. J. *J. Chem. Soc.* (1899) 75, p. 1066) the excess of racemate not neutralized by the resolving agent is neutralized by the addition of the necessary quantity of an achiral acid or base (depending on whether the resolving agent was an acid or base).

SUMMARY OF THE INVENTION

In one aspect, the present invention relates to a process for producing optically active compound of formula I or II:

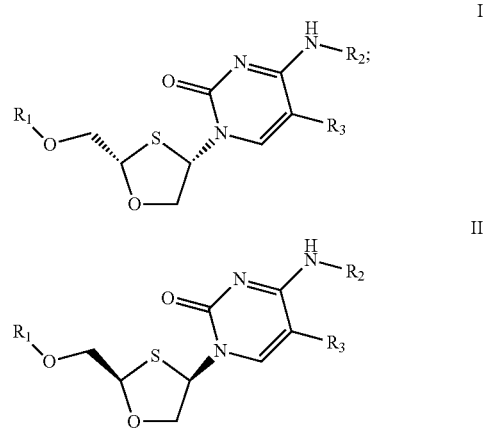

wherein;

$R_1$ is H, $C_{1-6}$ alkyl, $C_{6-12}$ aryl, $C_{6-12}$ arylalkyl (e.g., $C_{7-12}$ arylalkyl), $(CO)C_{1-6}$ alkyl, $(CO)O—C_{1-6}$ alkyl, $(CO)C_{6-12}$ aryl, or $(CO)C_{6-12}$ arylalkyl (e.g., $(CO)C_{7-12}$ arylalkyl);

$R_2$ is H, $C_{1-6}$ alkyl or $CO—R_5$; wherein $R_5$ is H or $C_{1-6}$ alkyl;

$R_3$ is H, $C_{1-6}$ alkyl, bromide, chloride, fluoride, iodide or $CF_3$; comprising:

a) reacting a compound of formula III in the cis configuration:

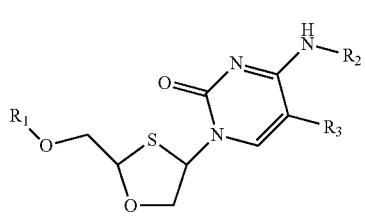

with a chiral acid to produce two diastereomeric salts;

b) recovering substantially one diastereomeric salt;

c) converting said one diastereomeric salt into said optically active compound.

In another aspect, there is provided a method for resolving a compound of formula III, in the cis configuration;

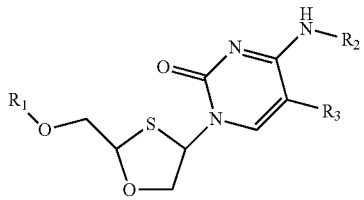

wherein:

$R_1$ is H, $C_{1-6}$ alkyl, $C_{6-12}$ aryl, $C_{6-12}$ arylalkyl (e.g. $C_{7-12}$ arylalkyl), (CO)$C_{1-6}$ alkyl, (CO)O—$C_{1-6}$ alkyl, (CO)O—$C_{6-12}$ aryl, or (CO)—$C_{6-12}$ arylalkyl (e.g., (CO)$C_{7-12}$arylalkyl);

$R_2$ is chosen from H, $C_{1-6}$ alkyl, $C_{1-6}$ acyl and CO—$R_5$; wherein $R_5$ is H or $C_{1-6}$ alkyl;

$R_3$ is H, $C_{1-6}$ alkyl, bromide, chloride, fluoride, iodide or $CF_3$; comprising:

a) reacting said compound of formula III with a chiral acid to produce two diastereomeric salts;
b) recovering substantially one diastereomeric salt;
c) converting said one diastereomeric salt into compound of formula I or II:

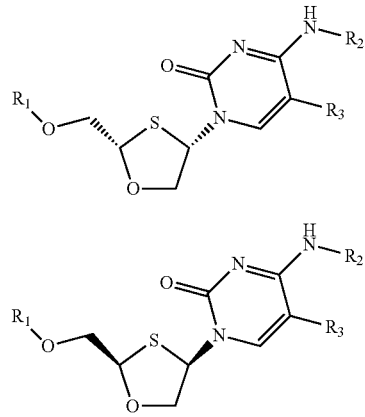

In a further aspect, the present invention provides a process for producing optically active cis-2-hydroxymethyl-4-(cytosin-1'-yl)-1,3-oxathiolane, comprising:

a) reacting a chiral acid with cis-2-hydroxymethyl-4-(cytosin-1'-yl)-1,3-oxathiolane to produce two diastereomeric salts;
b) recovering substantially one diastereomeric salt;
c) converting said one diastereomeric salt into said optically active cis-2-hydroxymethyl-4-(cytosin-1'-yl)-1,3-oxathiolane.

In still a further aspect, there is provided a process for producing (−)-cis-2-hydroxymethyl-4-(cytosin-1'-yl)-1,3-oxathiolane comprising:

a) reacting cis-2-hydroxymethyl-4-(cytosin-1'-yl)-1,3-oxathiolane with a half quantity molar amount of a chiral acid to substantially produce (−)-cis-2-hydroxymethyl-4-(cytosin-1'-yl) -1,3-oxathiolane•chiral acid salt, said molar ratio being with regard to cis-2-hydroxymethyl-4-(cytosin-1'-yl)-1,3-oxathiolane;

b) recovering said (−)-cis-2-hydroxymethyl-4-(cytosin-1'-yl)-1,3-oxathiolane•chiral acid salt;
c) converting said (−)-cis-2-hydroxymethyl-4-(cytosin-1'-yl)-1,3-oxathiolane•chiral acid salt into said (−)-cis-2-hydroxymethyl-4-(cytosin-1'-yl)-1,3-oxathiolane.

In still a further aspect, there is provided a process for producing optically active cis-2-hydroxymethyl-4-(cytosin-1'-yl)-1,3-oxathiolane, comprising:

a) reacting cis-2-hydroxymethyl-4-(cytosin-1'-yl)-1,3-oxathiolane with a chiral acid and an achiral acid to produce substantially one diastereomeric salt and substantially one enantiomeric salt;
b) recovering said diastereomeric salt;
c) converting said diastereomeric salt into optically active cis-2-hydroxymethyl-4-(cytosin-1'-yl)-1,3-oxathiolane.

In a further aspect, the present invention further provides novel cis-2-hydroxymethyl-4-(cytosin-1'-yl)-1,3-oxathiolane salts.

DETAILED DESCRIPTION OF THE INVENTION

Accordingly, the present invention relates to a process for producing optically active compound of formula I or II:

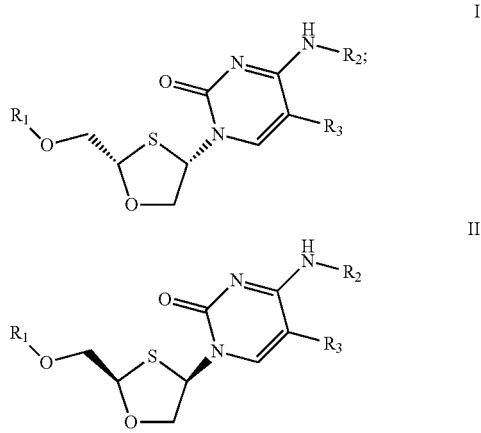

wherein:

$R_1$ is H, $C_{1-6}$ alkyl, $C_{6-12}$ aryl, $C_{6-12}$ arylalkyl (e.g., $C_{7-12}$ arylalkyl), (CO)$C_{1-6}$ alkyl, (CO)O—$C_{1-6}$ alkyl, (CO)$C_{6-12}$ aryl, or (CO)$C_{6-12}$ arylalkyl (e.g., (CO)$C_{7-12}$ arylalkyl);

$R_2$ is H, $C_{1-6}$ alkyl or CO—$R_5$; wherein $R_5$ is H or $C_{1-6}$ alkyl;

$R_3$ is H, $C_{1-6}$ alkyl, bromide, chloride, fluoride, iodide or $CF_3$; comprising:

a) reacting a compound of formula III in the cis configuration:

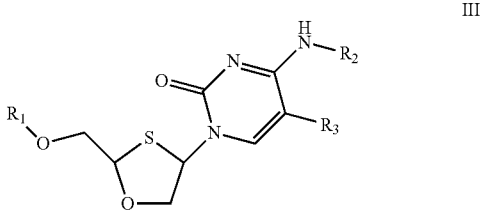

with a chiral acid to produce two diastereomeric salts;
b) recovering substantially one diastereomeric salt;
c) converting said one diastereomeric salt into said optically active compound.

The scope the present invention includes a process as described above wherein the over-all yield of the desired enantiomer is equal to or greater than 25% (100 g of racemate would produce at least 25 g of the desired enantiomer).

An embodiment of the present invention relates to a process which generates a final product which is substantially in the form of a single enantiomer. Additionally, an embodiment of the present invention includes a process described above which results in a product having an enantiomeric excess of 99% or higher.

An embodiment of the present invention relates to a process for producing optically active compound of formula I or II:

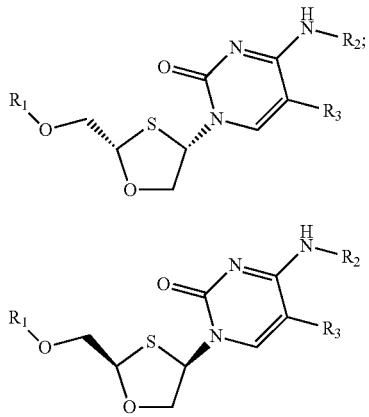

I

II wherein: $R_1$, $R_2$, $R_3$ are as defined above, comprising:
a) reacting a compound of formula III in the cis configuration:

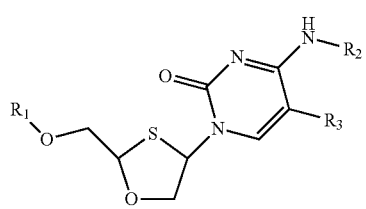

III with a chiral acid to produce two diastereomeric salts;
b) recovering substantially one diastereomeric salt;
c) converting said one diastereomeric salt into said optically active compound.

There is also provided a method for resolving a compound of formula III, in the cis configuration:

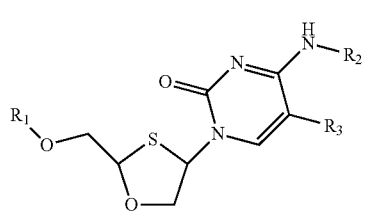

III wherein: $R_1$, $R_2$, $R_3$ are as defined above, comprising:
a) reacting said compound of formula III with a chiral acid to produce two diastereomeric salts;
b) recovering substantially one diastereomeric salt;
c) converting said one diastereomeric salt into a compound of formula I or II:

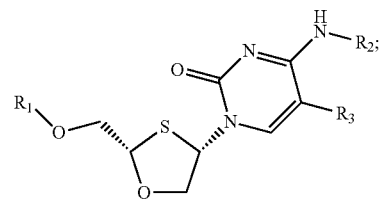

I

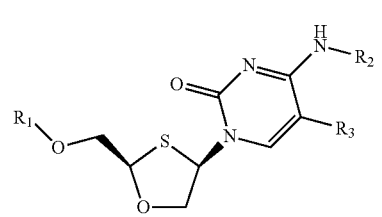

II

In one embodiment, $R_1$ is H, $C_{1-6}$ alkyl, (CO)$C_{1-6}$ alkyl, (CO)O—$C_{1-6}$ alkyl or (CO)$C_{6-12}$ aryl.

In further embodiments:
$R_1$ is H, (CO)$C_{1-6}$ alkyl or (CO)$C_{6-12}$ aryl,
$R_1$ is H,
$R_1$ is (CO)$C_{6-12}$ aryl.

Still in further embodiments:
$R_2$ is H or $C_{1-6}$ alkyl,
$R_2$ is CO—$R_5$, wherein $R_5$ is H or $C_{1-6}$ alkyl,
$R_2$ is formyl or acetyl.

In one embodiment, $R_3$ is H, $C_{1-6}$ alkyl or fluoride.

In further embodiments:
$R_3$ is H or fluoride,
$R_3$ is H,
$R_3$ is fluoride.

In one embodiment, the chiral acid is (1R)-(−)-10-camphorsulfonic acid, (−)-2,3-dibenzoyl-L-tartaric acid, (+)-L-tartaric acid or (−)-L-malic acid.

In one embodiment, the chiral acid is (1R)-(−)-10-camphorsulfonic acid.

In another embodiment, the optically active compound is

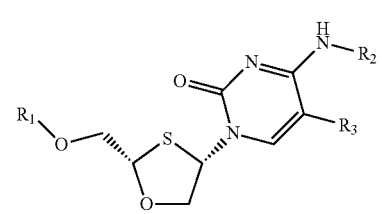

I

In another embodiment, the optically active compound is

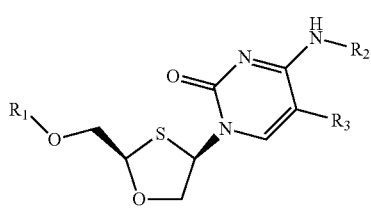

In one embodiment, the two diastereomeric salts comprise a first more soluble diastereomeric salt and a second less soluble diastereomeric salt.

In a further embodiment, step b) described above further comprises recovering a second diastereomeric salt.

The present invention further provides a process for producing optically active compound of formula IV:

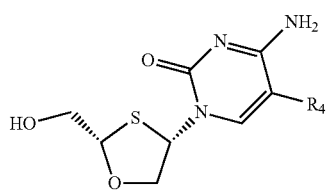

wherein:
$R_4$ is H or fluoride; comprising:
a) reacting a compound of formula III in the cis configuration:

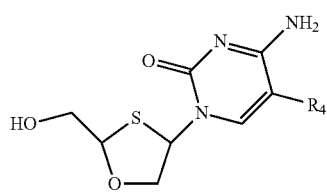

with a chiral acid selected from (1R)-(−)-10-camphorsulfonic acid, (−)-2,3-dibenzoyl-L-tartaric acid, (+)-L-tartaric acid or (−)-L-malic acid, to produce two diastereomeric salts;
b) recovering substantially one diastereomeric salt;
c) converting said one diastereomeric salt into said optically active compound.

In one aspect, there is provided a process for producing optically active cis-2-hydroxymethyl-4-(cytosin-1'-yl)-1,3-oxathiolane, comprising:
a) reacting a chiral acid with cis-2-hydroxymethyl-4-(cytosin-1'-yl)-1,3-oxathiolane to produce two diastereomeric salts;
b) recovering substantially one diastereomeric salt;
c) converting said one diastereomeric salt into said optically active cis-2-hydroxymethyl-4-(cytosin-1'-yl)-1,3-oxathiolane.

In one embodiment, the optically active cis-2-hydroxymethyl-4-(cytosin-1'-yl)-1,3-oxathiolane is crystalline.

In one embodiment, the optically active cis-2-hydroxymethyl-4-(cytosin-1'-yl)-1,3-oxathiolane is the (−) enantiomer.

In one embodiment, the optically active cis-2-hydroxymethyl-4-(cytosin-1'-yl)-1,3-oxathiolane is the (+) enantiomer.

In one embodiment, the chiral acid is (1R)-(−)-10-camphorsulfonic acid, (−)-2,3-dibenzoyl-L-tartaric acid, (+)-L-tartaric acid or (−)-L-malic acid.

In one embodiment, the chiral acid is (1R)-(−)-10-camphorsulfonic acid.

In one embodiment, the optically active cis-2-hydroxymethyl-4-(cytosin-1'-yl)-1,3-oxathiolane has an enantiomeric excess of 60% or higher.

In one embodiment, the optically active cis-2-hydroxymethyl-4-(cytosin-1'-yl)-1,3-oxathiolane has an enantiomeric excess of 70% or higher.

In one embodiment, the optically active cis-2-hydroxymethyl-4-(cytosin-1'-yl)-1,3-oxathiolane has an enantiomeric excess of 80% or higher.

In one embodiment, the optically active cis-2-hydroxymethyl-4-(cytosin-1'-yl)-1,3-oxathiolane has an enantiomeric excess of 90% or higher.

In one embodiment, the optically active cis-2-hydroxymethyl-4-(cytosin-1'-yl)-1,3-oxathiolane has an enantiomeric excess of 95% or higher.

In one embodiment, the optically active cis-2-hydroxymethyl-4-(cytosin-1'-yl)-1,3-oxathiolane has an enantiomeric excess of 98% or higher.

In one embodiment, the optically active cis-2-hydroxymethyl-4-(cytosin-1'-yl)-1,3-oxathiolane has an enantiomeric excess of 99% or higher.

In one aspect, there is provided a process for producing (−)-cis-2-hydroxymethyl-4-(cytosin-1'-yl)-1,3-oxathiolane•chiral acid salt, comprising:
a) reacting cis-2-hydroxymethyl-4-(cytosin-1'-yl)-1,3-oxathiolane with a chiral acid to produce (−)-cis-2-hydroxymethyl-4-(cytosin-1'-yl)-1,3-oxathiolane•chiral acid salt and (+)-cis-2-hydroxymethyl-4-(cytosin-1'-yl)-1,3-oxathiolane•chiral acid salt;
b) recovering said (−)-cis-2-hydroxymethyl-4-(cytosin-1'-yl)-1,3-oxathiolane•chiral acid salt.

In one embodiment, said step b) further comprises recovering (+)-cis-2-hydroxymethyl-4-(cytosin-1'-yl)-1,3-oxathiolane•chiral acid salt.

In one embodiment, said (−)-cis-2-hydroxymethyl-4-(cytosin-1'-yl)-1,3-oxathiolane•chiral acid salt contains less than 30% of (+)-cis-2-hydroxymethyl-4- (cytosin-1'-yl)-1,3-oxathiolane•chiral acid salt.

In further embodiments:
(−)-cis-2-hydroxymethyl-4-(cytosin-1'-yl)-1,3-oxathiolane•chiral acid salt contains less than 20% of (+)-cis-2-hydroxymethyl-4-(cytosin-1'-yl)-1,3-oxathiolane•chiral acid salt;

(−)-cis-2-hydroxymethyl-4-(cytosin-1'-yl)-1,3-oxathiolane•chiral acid salt contains less than 10% of (+)-cis-2-hydroxymethyl-4-(cytosin-1'-yl)-1,3-oxathiolane•chiral acid salt;

(−)-cis-2-hydroxymethyl-4-(cytosin-1'-yl)-1,3-oxathiolane•chiral acid salt contains less than 5% of (+)-cis-2-hydroxymethyl-4-(cytosin-1'-yl)-1,3-oxathiolane•chiral acid salt;

(−)-cis-2-hydroxymethyl-4-(cytosin-1'-yl)-1,3-oxathiolane•chiral acid salt contains less than 1% of (+)-cis-2-hydroxymethyl-4-(cytosin-1'-yl)-1,3-oxathiolane•chiral acid salt;

(−)-cis-2-hydroxymethyl-4-(cytosin-1'-yl)-1,3-oxathiolane•chiral acid salt is substantially free of (+)-cis-2-hydroxymethyl-4-(cytosin-1'-yl)-1,3-oxathiolane•chiral acid salt.

In one embodiment, the process further comprises recrystallizing said (−)-cis-2-hydroxymethyl-4-(cytosin-1′-yl)-1,3-oxathiolane•chiral resolving acid addition salt.

In one embodiment, said chiral acid is in stoichiometric molar ratio with regard cis-2-hydroxymethyl-4-(cytosin-1′-yl)-1,3-oxathiolane.

In one embodiment, said chiral acid is in nonstoichiometric molar ratio with regard to cis-2-hydroxymethyl-4-(cytosin-1′-yl)-1,3-oxathiolane.

In one aspect, there is provided a process for producing (−)-cis-2-hydroxymethyl-4-(cytosin-1′-yl)-1,3-oxathiolane comprising:
  a) reacting cis-2-hydroxymethyl-4-(cytosin-1′-yl)-1,3-oxathiolane with a half-quantity molar amount of a chiral acid to substantially produce (−)-cis-2-hydroxymethyl-4-(cytosin-1′-yl)-1,3-oxathiolane•chiral acid salt, said molar ratio being with regard to cis-2-hydroxymethyl-4-(cytosin-1′-yl)-1,3-oxathiolane;
  b) recovering said (−)-cis-2-hydroxymethyl-4-(cytosin-1′-yl)-1,3-oxathiolane•chiral acid salt;
  c) converting said (−)-cis-2-hydroxymethyl-4-(cytosin-1′-yl)-1,3-oxathiolane•chiral acid salt into said (−)-cis-2-hydroxymethyl-4-(cytosin-1′-yl)-1,3-oxathiolane In one embodiment, said step a) further comprise adding a half-quantity molar amount of achiral acid to substantially produce (+)-cis-2-hydroxymethyl-4-(cytosin-1′-yl)-1,3-oxathiolane•achiral acid salt, said molar ratio being with regard to cis-2-hydroxymethyl-4-(cytosin-1′-yl)-1,3-oxathiolane.

In one embodiment, said chiral acid is (1R)-(−)-10-camphorsulfonic acid, (−)-2,3-dibenzoyl-L-tartaric acid, (+)-L-tartaric acid or (−)-L-malic acid.

In one embodiment, said chiral acid is (1R)-(−)-10-camphorsulfonic acid.

In one embodiment, said achiral acid is hydrochloric acid.

In a further aspect, there is provided a process for producing crystalline optically active cis-2-hydroxymethyl-4-(cytosin-1′-yl)-1,3-oxathiolane, comprising:
  a) reacting cis-2-hydroxymethyl-4-(cytosin-1′-yl)-1,3-oxathiolane with a chiral acid and an achiral acid to produce substantially one diastereomeric salt and substantially one enantiomeric salt;
  b) recovering said diastereomeric salt;
  c) converting said diastereomeric salt into optically active cis-2-hydroxymethyl-4-(cytosin-1′-yl)-1,3-oxathiolane.

An embodiment of the process of the present invention generates an over-all yield equal to or greater than 25% of the desired enantiomer.

An additional embodiment of the process of the present invention generates the desired enantiomer with an enantiomeric excess of 95% or higher.

Another embodiment of the process of the present invention generates an over-all yield equal to or greater than 25% of the desired enantiomer and an enantiomeric excess of 99% or higher.

In one embodiment, said diastereomeric salt is (−)-cis-2-hydroxymethyl-4-(cytosin-1′-yl)-1,3-oxathiolane•(1R)-(−)-10-camphorsulfonate.

In one embodiment, said enantiomeric salt is (+)-cis-2-hydroxymethyl-4-(cytosin-1′-yl)-1,3-oxathiolane•hydrochloric acid salt.

An "oxathiolane ring" is any substituted or unsubstituted five member monocyclic ring that has an oxygen atom in position 1 and a sulfur atom in position 3 of the ring as illustrated below:

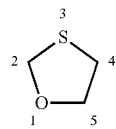

It will be apparent to a skilled person in the field that the reaction conditions described in these examples may be modified and still achieve successful results.

Typically, solvents, temperature and time of reaction may be varied. A suitable solvent will allow the process to occur under the reaction conditions without adversely affecting the reaction. The solvent may be one or more solvents and may be organic (e.g., methanol, ethanol, propanol, isopropanol, dichloromethane, dichloroethane, tetrahydrofuran, hexane, pentane, ether spirit, ethyl ether), water or aqueous/organic (e.g., methanol-water, isopropanol-water). The solvents may also be present in various ratios (for example 1:1, 2:1, 5:1, 10:1 or 1:1:1, 1:2:1).

The temperature may be varied and will allow the process to occur under the reaction conditions. The suitable temperature will provide the desired product without adversely affecting the reaction.

It will be appreciated by a person of skill in the art that a suitable period of time is a time for obtaining a sufficient chemical transformation of the starting material, obtaining the desired purity or the desired yield of the reaction product or a combination of those. The reaction can typically be monitored, if desired, by thin layer chromatography, light absorption (e.g., U.V.) of reaction medium, gas chromatography or high performance liquid chromatography (HPLC)

Cis-2-Hydroxymethyl-4-(cytosin-1′-yl)-1,3-oxathiolane exist as

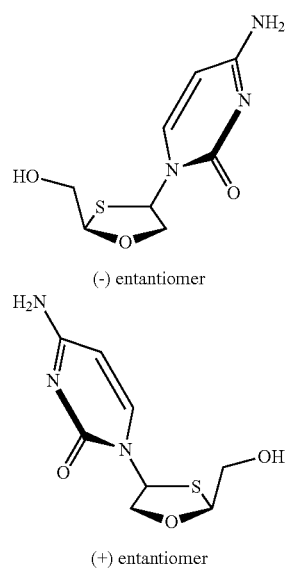

enantiomers which may be in various ratios.

For example the enantiomers may be present as racemate (i.e. in equal proportions) or any alternative ratio of the enantiomers such as for example 1:1, 2:1, 5:1, 10:1, 100:1 or 1:2, 1:5, 1:10, 1:100. References hereinafter to cis-2-Hydroxymethyl-4-(cytosin-1′-yl)-1,3-oxathiolane according to the invention includes all such possible ratios of enantiomers.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents a straight chain or branched chain hydrocarbon moiety which may optionally be substituted by one or more of halogen, nitro, nitroso, sulfate, sulfate ester, sulfonate, sulfonate ester, phosphonate ester, amide, $C_{1-6}$ alkyl, $C_{6-12}$ aralkyl (e.g., $C_{7-12}$ aralkyl), $C_{6-12}$ aryl, $C_{1-6}$ alkyloxy, $C_{6-12}$ aryloxy, C(O)—$C_{1-6}$ alkyl, C(O)—$C_{6-12}$ aryl, C(O)$C_{6-12}$ aralkyl (e.g., C(O)$C_{7-12}$ aralkyl), heterocycle having 3-10 ring-members, hydroxyl, amino, ester, cyano, azido, amidino or guanido. Useful examples of alkyl include isopropyl, propyl, ethyl, methyl, hexyl or cyclopropyl, which in each case is unsubstituted or substituted one or more times by, for example, halogen, nitro, nitroso, sulfate, sulfonate, amide, hydroxyl, amino, ester, cyano, azido, amidino or guanido. The term alkyl is also meant to include alkyl in which one or more hydrogen atoms are each replaced by a halogen, preferably fluoro (e.g., $CF_3$— or $CF_3CH_2$—).

The term "aryl" represents a carbocyclic moiety containing at least one benzenoid-type ring which may optionally be substituted by one or more of halogen, nitro, nitroso, sulfate, sulfate ester, sulfonate, sulfonate ester, phosphonate ester, amide, $C_{1-6}$ alkyl, $C_{6-12}$ aralkyl, $C_{6-12}$ aryl, $C_{1-6}$ alkyloxy, $C_{6-12}$ aryloxy, C(O)—$C_{1-6}$ alkyl, O(O)—$C_{6-12}$ aryl, C(O)$C_{6-12}$ aralkyl, heterocycle having 3-10 ring-members, hydroxyl, amino, ester, cyano, azido, amidino or guanido. Examples of aryl include phenyl and naphthyl, which in each case is unsubstituted or substituted one or more times by, for example, halogen, nitro, nitroso, sulfate, sulfonate, amide, hydroxyl, amino, ester, cyano, azido, amidino or guanido.

The term "aralkyl" represents an aryl group attached to the adjacent atom by an alkyl. Useful examples include benzyl which is unsubstituted or substituted one or more times by, for example, halogen, nitro, nitroso, sulfate, sulfonate, amide, hydroxyl, amino, ester, cyano, azido, amidino or guanido.

The term "heterocycle" represents a saturated or unsaturated, cyclic moiety wherein said cyclic moiety is interrupted by at least one heteroatom, (e.g., oxygen, sulfur or nitrogen) which may optionally be substituted by one or more of halogen, nitro, nitroso, sulfate, sulfate ester, sulfonate, sulfonate ester, phosphonate ester, amide, $C_{1-6}$ alkyl, $C_{6-12}$ aralkyl, $C_{6-12}$ aryl, $C_{1-6}$ alkyloxy, $C_{6-12}$ aryloxy, C(O)—$C_{1-6}$ alkyl, C(O)—$C_{6-12}$ aryl, C(O)$C_{6-12}$ aralkyl, hydroxyl, amino, ester, cyano, azido, amidino or guanido. It is understood that the term heterocyclic ring represents a mono or polycyclic (e.g., bicyclic) ring. Examples of heterocyclic rings include but are not limited to epoxide; furan; benzofuran; isobenzofuran; oxathiolane; dithiolane; dioxolane; pyrrole; pyrrolidine; imidazole; pyridine; pyrimidine; indole; piperidine; morpholine; thiophene and thiomorpholine, which in each case is unsubstituted or substituted one or more times by, for example, halogen, nitro, nitroso, sulfate, sulfonate, amide, hydroxyl, amino, ester, cyano, azido, amidino or guanido.

The term "independently" means that a substituent can be the same or different definition for each item.

The term "optically active" means that the enantiomeric excess is greater than zero.

The optical purity is numerically equivalent to the "enantiomeric excess". The term "enantiomeric excess" or "ee" is defined in percentage (%) value as follows: [mole fraction (major enantiomer)−mole fraction (minor enantiomer)]×100. (for example, an ee of 99% represent a ratio of 99.5% of one enantiomer and 0.5% of the opposite enantiomer).

The term "chiral acid" means an optically active acidic compound able to form a diastereomer with a compound of formula III, such as 2-hydroxymethyl-4-(cytosin-1'-yl)-1,3-oxathiolane. Examples of such acids include without limitation: tartaric acid, O,O'-dibenzoyltartaric acid, O,O'-di-p-toluoyltartaric acid, 2-nitrotartranilic acid, mandelic acid, malic acid, 2-phenoxypropionic acid, 10-camphorsulfonic acid, hydratropic acid, N-acetylleucine, N-(α-methylbenzyl) succinamic acid, N-(α-methylbenzyl)phthamic acid, 3-bromocamphor-9-sulfonic acid, camphor-3-sulfonic acid, quinic acid, di-O-isopropylidene-2-oxo-L-gulonic acid, lasalocid, 1,1'-binaphthyl-2,2/-phosphoric acid, cholestenonesulfonic acid. Further examples include (1R)-(−)-10-camphorsulfonic acid, (−)-2,3-dibenzoyl-L-tartaric acid, (+)-L-tartaric acid and (−)-L-malic acid.

A person of ordinary skill will understand that the term "achiral acid" includes a variety of acids such as inorganic acids (e.g., HCl, HBr, $H_2SO_4$, $HBF_4$); sulfonic acids (e.g., methanesulfonic, benzenesulfonic, p-toluenesulfonic, p-hydroxytoluenesulfonic, sulfanilic, p-chlorobenezenesulfonic); substituted acetic acids (e.g., glycolic, chloro-, dichloro-, trichloroacetic); polycarboxylic and oxy acids (e.g., succinic, adipic, maleic, fumaric, citric, pyruvic).

There are also provided pharmaceutically acceptable salts of the compounds of the present invention. By the term "pharmaceutically acceptable salts" is meant salts derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic, cysteic acid and benzenesulphonic acids. Other acids such as oxalic, while not themselves pharmaceutically acceptable, may be useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and $NR_4^+$ (where R is $C_{1-4}$ alkyl) salts.

References hereinafter to a compound according to the invention include the compound and its pharmaceutically acceptable salts.

Dowex® Marathon A-OH is a trade-mark of DOW Chemical Company.

In one aspect, the present invention provides novel compounds as described in table 1:

TABLE 1

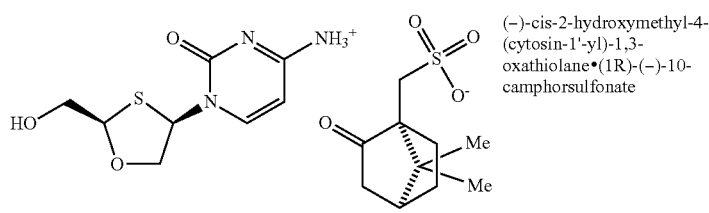

(−)-cis-2-hydroxymethyl-4-(cytosin-1'-yl)-1,3-oxathiolane•(1R)-(−)-10-camphorsulfonate

TABLE 1-continued

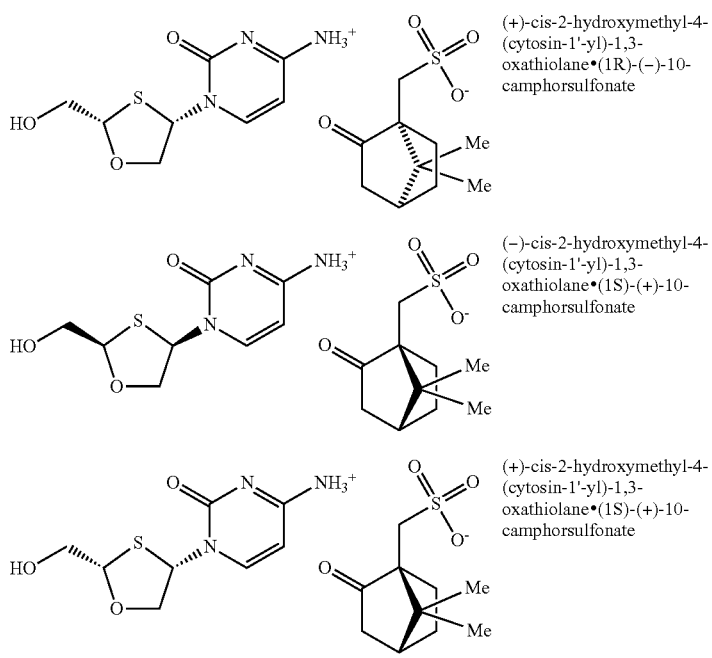

In one embodiment, the process and method of the present invention comprises those wherein the following embodiments are present, either independently or in combination.

The entire disclosures of all applications, patents and publications, cited above and below, are hereby incorporated by reference.

EXAMPLES

The following examples are provided to illustrate various embodiments of the present invention and shall not be considered as limiting in scope.

Example 1

Screening of Chiral Resolving Agents

Experimental Conditions:
100 mg of cis-2-Hydroxymethyl-4-(cytosin-1'-yl)-1,3-oxathiolane is combined with 1 equivalent of the resolving agent, in 1 ml of solvent (95% ethanol-5% water). The solid is isolated and weighed. A significant test requires that the weight of crystals does not exceed 50% of the overall diastereomer amount. If this condition is not fulfilled the amount or type of solvent is changed.

TABLE 2

| Chiral Resolving Agent | No crystal Observed | Crystal Observed |
|---|---|---|
| (−)-L-Malic acid | | x |
| (−)-L-Lactic acid | X (oil) | |
| (+)-L-Tartaric acid | | x |
| (−)-2,3-Dibenzoyl-L-Tartaric acid | | x |
| (1R)-(−)-10-Camphorsulfonic acid | | x |

Example 2

Resolution Experimentations

General Experimental Conditions:
cis-2-Hydroxymethyl-4-(cytosin-1'-yl)-1,3-oxathiolane, and a chiral acid were dissolved with stirring in a solvent at a temperature of about room temperature to about 50° C. and then cooled at a temperature of between about room temperature to −10° C. for 2-4 hours. The solid product was collected by filtration. The composition was determined by Chiral HPLC, the aqueous buffer was prepared by diluting 0.5 ml triethylamine in 1 L HPLC water, the pH adjusted to 6.88 with glacial acetic acid. The mobile phase was prepared by combining the aqueous buffer and methanol in a ratio of 90:10 and the gas was removed. The following conditions were used:

Column: Astec Cyclobond I 2000 RSP, 5 micron, 250×4.5 mm.
Guard column: Astec Cyclobond I 2000 RSP, 20×4.0 mm
Flow: 0.6 ml/min.
Sample preparation: prepare solution of 0.5 mg/ml in mobile phase.
Injection volume: 5 μL.
Mode: isocratic.
UV-Vis detector at: 270 nm.
Column temperature: 0° C.
Run time: 40 min.

TABLE 3

| | Chiral resolving agent/achiral acid | Solvent | Experimental Conditions | Enantiomeric Ratio (yield %) |
|---|---|---|---|---|
| 1 | L-tartaric acid (0.5 eq)/HCl (0.5 eq.) | Isopropyl alcohol and water 1:1 (v/v) | 100 g scale. Magnetic stirring. | 45.2:52.1 (63%) |

TABLE 3-continued

| Chiral resolving agent/achiral acid | Solvent | Experimental Conditions | Enantiomeric Ratio (yield %) |
|---|---|---|---|
| 2 (R)-Camphorsulfonic Acid (0.5 eq)/ HCl (0.5 eq.) | Isopropyl alcohol and water 1:1 (v/v) | 5 g scale. Heated @50° C. to dissolve solids Magnetic stirring | 92.4:7.6 (36%) |
| 3 (−)-2,3-Dibenzoyl-L-Tartaric acid (0.25 eq)/HCl (0.5 eq.) | Water | 5 g scale. Magnetic stirring | 47.6:45.7 (41.7%) |
| 4 (R)-Camphorsulfonic Acid (0.5 eq)/ HCl (0.5 eq.) | Isopropyl alcohol and water 1:1 (v/v) | 25 g scale. Mechanical stirring | 90.9:9.1 (52.6%) |
| 5 (R)-Camphorsulfonic Acid (0.5 eq)/ HCl (0.5 eq.) | Water Methanol 17% water in methanol (v/v) | 5 g scale. Heated at reflux. Magnetic stirring | 78.7:21.3 (72%) |
| 6 (R)-Camphorsulfonic Acid (1 eq)/no achiral acid | Isopropyl alcohol and water 1:1 (v/v) | 5 g scale. Heated @50° C. to dissolve solids Magnetic stirring | 53.5:46.4 (60.6%) |

Scheme 1

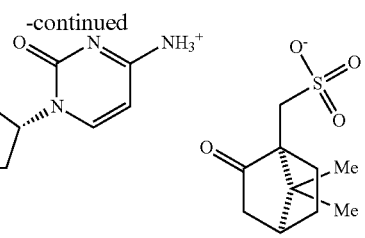

Example 3

Diastereomeric salt optical resolution of cis-2-Hydroxymethyl-4-(cytosin-1'-yl)-1,3-oxathiolane cis-2-Hydroxymethyl-4-(cytosin-1'-yl)-1,3-oxathiolane (1.03 g, 4.3 mmol), and (1R)-(−)-10-Camphorsulfonic acid (1.03 g, 4.3 mmol) were dissolved in 32 mL of a 1:1 isopropyl alcohol and water (v/v) at 50° C. The solution was cooled at 0° C. The solid was filtered to provide 0.55 g of dry crystals. The diastereomeric composition was determined by HPLC to be 87:13 [(−)-cis-2-hydroxymethyl-4-(cytosin-1'-yl)-1,3-oxathiolane•(1R)-(−)-10-camphorsulfonic salt: (+)-cis-2-hydroxymethyl-4-(cytosin-1'-yl)-1,3-oxathiolane•(1R)-(−)-10-camphorsulfonic salt)].

The mother liquor was concentrated to dryness giving 1.38 g of dry solids with a diastereomeric composition of 35:65 [(−)-cis-2-hydroxymethyl-4-(cytosin-1'-yl)-1,3-oxathiolane•(1R)-(−)-10-camphorsulfonic salt: (+)-cis-2-hydroxymethyl-4-(cytosin-1'-yl)-1,3-oxathiolane•(1R)-(−)-10-camphorsulfonic salt)]. The composition was analyzed as shown in Example 2.

Example 4

Recrystallization to increase the diastereomeric ratio of (−)-cis-2-hydromethyl-4-(cytosin-1'-)-1,3-oxathiolane•(1R)-(−)-10-camphorsulfonic salt with reward to (+)-cis-2-hydroxymethyl-4-(cytosin-1'-yl)-1,3-oxathiolane•(1R)-(−)-10-Camphorsulfonic salt The crude cis-2-hydroxymethyl-4-(cytosin-1'-yl)-1,3-oxathiolane•(1R)-(−)-10-camphorsulfonate salt generated in entry 4 of table 3 in example 2 having an enantiomeric ratio of 90.9:9.1 [(−)-cis-2-hydroxymethyl-4-(cytosin-1'-yl)-1,3-oxathiolane•(1R)-(−)-10-camphorsulfonic salt: (+) -cis-2-hydroxymethyl-4-(cytosin-1'-yl)-1,3-oxathiolane•(1R)-(−)-10-camphorsulfonic salt] was dissolved in isopropyl alcohol-water 1:1 (v/v) at 70° C. After cooling, the crystals were recovered with a yield of 76% and an enantiomeric ratio of 99.1:0.9 [(−)-cis-2-hydroxymethyl-4-(cytosin-1'-yl)-1,3-oxathiolane•(1R)-(−)-10-camphorsulfonic salt: (+)-cis-2-hydroxymethyl-4-(cytosin-1'-yl)-1,3-oxathiolane•(1R)-(−)-10-camphorsulfonic salt].

Example 5

Kilogram-Scale Diastereomeric Salt Optical Resolution

A mixture of isopropanol (2274 kg), distilled water (2905 kg), cis-2-Hydroxymethyl-4-(cytosin-1'-yl)-1,3-oxathiolane (193.7 kg) were introduced into the reactor (model R06 5700L GLMS). Dilute hydrochloric acid (prepared as 41.57 kg in 380 kg of water) was introduced followed by (1R)-(−)-10-camphorsulfonic acid (100 kg). The temperature of the resulting slurry was adjusted to 50° C. and agitated until all solid dissolved. The solution was then cooled to about −10° C. (−13° C. to −7° C.) and agitated for 4-6 hours.

The resulting slurry is filtered, rinsing forward with 60 L of 1:1 isopropyl alcohol and water (v/v). The product is pulled dry with enantiomeric ratio of 91.9 [(−)-cis-2-hydroxymethyl-4-(cytosin-1'-yl)-1,3-oxathiolane•(1R)-(−)-10-camphorsulfonic salt: (+)-cis-2-hydroxymethyl-4-(cytosin-1'-yl)-1,3-oxathiolane•(1R)-(−)-10-camphorsulfonic salt)].

Isopropanol (228 kg) and water (291 kg) are added to the wet crude product then the temperature of the resulting solution was adjusted to 70° C. and agitated until all solid dissolved the slurry is heated and agitated until all the solids dissolve. The solution is then cooled to about 22° C. (19° C. to 25° C.) and then to 0° C. (−3° C. to 3° C.)

The resulting slurry is filtered, rinsing forward with two portions of 70 L of 1:1 isopropyl alcohol and water (v/v). The product is spin-dried until the flow of filtrate essentially stops. 90.8 kg of product recovered (87% yield, corrected for loss on dryness of a sample) with an enantiomeric purity higher than 98%.

Scheme 2

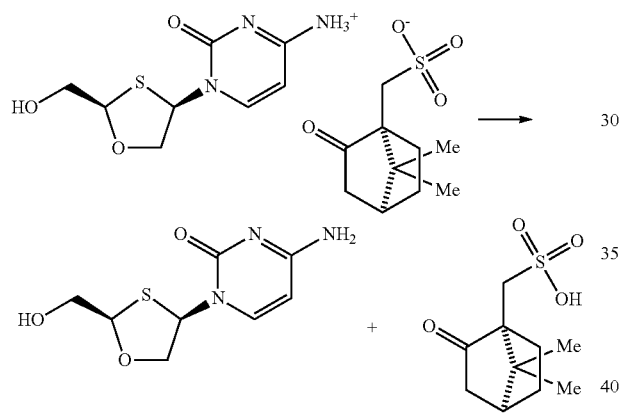

Example 6

(1R)-(−)-10-camphorsulfonic acid removal from (−)-cis-2-hydroxymethyl-4-(cytosin-1'-yl)-1,3-oxathiolane•(1R)-(−)-10-camphorsulfunic salt (−)-cis-2-hydroxymethyl-4-(cytosin-1'-yl)-1,3-oxathiolane•(1R)-(−)-10-Camphorsulfonic salt (90.8 kg) is dissolved in methanol (601 kg) by heating the mixture at 40° C. and agitating until a solution is achieved.

The warm solution is circulated through an ion exchange column containing Dowex® Marathon A-OH (133.6 kg) and methanol (200 kg) of while maintaining the temperature at 40° C. until no residual camphorsulfonic acid is detected by NMR analysis and pH is greater than 7 (measured using water-wet pH paper).

The eluent is filtered, rinsing forward with methanol (200 kg).

The filtrate is partially concentrated under vacuum to about 140 L.

The concentrate is cooled to about −10° C. for one hour and agitated. The resulting slurry is filtered, rinsing forward with 2 portions of 18 kg of cold methanol (−10° C.). The product is dried under vacuum while heating to 35-40° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claims:

1. A process for producing an optically active compound of formula I or formula II:

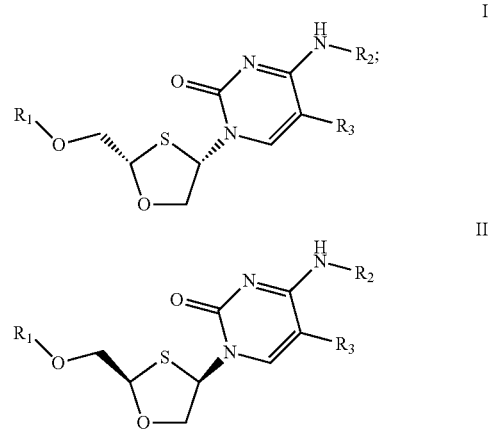

wherein:
R₁ is H, $C_{1-6}$alkyl, $C_{6-12}$aryl, $C_{6-12}$arylalkyl, (CO)$C_{1-6}$alkyl, (CO)O—$C_{1-6}$alkyl, (CO)$C_{6-12}$aryl, or (CO)$C_{6-12}$arylalkyl;
R₂ is H, $C_{1-6}$alkyl or CO—R₅;
R₃ is H, $C_{1-6}$alkyl, bromide, chloride, fluoride, iodide or CF₃; and
R₅ is H or $C_{1-6}$alkyl;
said process comprising:
a) reacting a compound of formula III in the cis configuration:

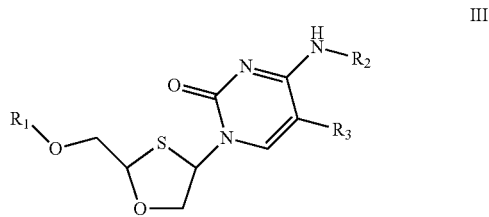

with a chiral acid to produce a mixture of two diastereomeric salts, wherein said chiral acid is (1R)-(−)-10-camphorsulfonic acid, (−)-2,3-dibenzoyl-L-tartaric acid, (+)-L-tartaric acid or (−)-L-malic acid;
b) recovering a mixture of said two diastereomeric salts containing an excess of one of said two diastereomeric salts;
c) converting said one of said two diastereomeric salts into said optically active compound of formula I or formula II.

2. A process according to claim 1, wherein $R_1$ is H, $C_{1-6}$alkyl, $(CO)C_{1-6}$alkyl, $(CO)O-C_{1-6}$alkyl or $(CO)C_{6-12}$aryl.

3. A process according to claim 1, wherein $R_1$ is H, $(CO)C_{1-6}$alkyl or $(CO)C_{6-12}$aryl.

4. A process according to claim 1, wherein $R_2$ is H, $C_{1-6}$alkyl, or $CO-R_5$, wherein $R_5$ is H or $C_{1-6}$alkyl.

5. A process according to claim 1, wherein $R_2$ is formyl or acetyl.

6. A process according to claim 1, wherein $R_3$ is H, $C_{1-6}$alkyl or fluoride.

7. A process according to claim 1, wherein said chiral acid is (1R)-(−)-10-camphorsulfonic acid.

8. A process according to claim 1, wherein said optically active compound is a compound of formula I:

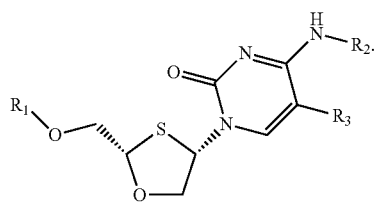

I

9. A process according to claim 1, wherein said optically active compound is a compound of formula II:

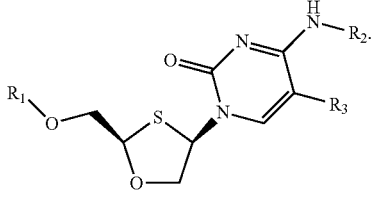

II

10. A process according to claim 1, wherein said two diastereomeric salts comprise a first more soluble diastereomeric salt and a second less soluble diastereomeric salt.

11. A process according to claim 1, wherein said optically active compound of is an optically active compound of formula IV:

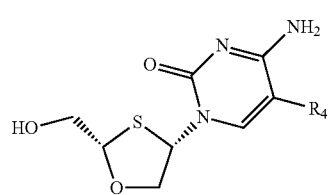

IV wherein $R_4$ is H or fluoride.

12. A method for resolving a compound of formula III, in the cis configuration:

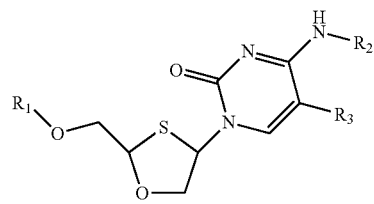

III wherein:
$R_1$ is H, $C_{1-6}$alkyl, $C_{6-12}$aryl, $C_{6-12}$arylalkyl, $(CO)C_{1-6}$alkyl, $(CO)O-C_{1-6}$alkyl, $(CO)C_{6-12}$aryl, or $(CO)C_{6-12}$arylalkyl;
$R_2$ is H, $C_{1-6}$alkyl or $CO-R_5$;
$R_3$ is H, $C_{1-6}$alkyl, bromide, chloride, fluoride, iodide or $CF_3$; and
$R_5$ is H or $C_{1-6}$alkyl;
said process comprising:
 a) reacting said compound of formula III with a chiral acid to produce two diastereomeric salts, wherein said chiral acid is (1R)-(−)-10-camphorsulfonic acid, (−)-2,3-dibenzoyl-L-tartaric acid, (+)-L-tartaric acid or (−)-L-malic acid;
 b) recovering a mixture of said two diastereomeric salts containing an excess of one of said two diastereomeric salts;
 c) converting said one of said two diastereomeric salts into a compound of formula I or II:

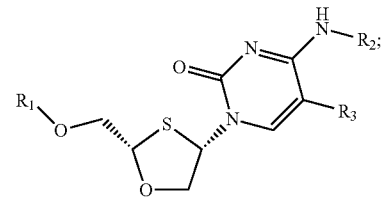

I

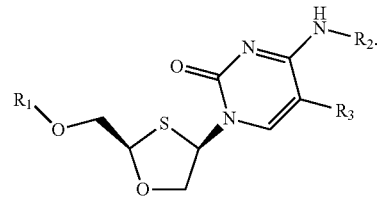

II

13. A method according to claim 12, wherein $R_1$ is H, $C_{1-6}$alkyl, $(CO)C_{1-6}$alkyl, $(CO)O-C_{1-6}$alkyl or $(CO)C_{6-12}$aryl.

14. A method according to claim 12, wherein $R_2$ is H, $C_{1-6}$alkyl or $CO-R_5$, wherein $R_5$ is H or $C_{1-6}$alkyl.

15. A method according to claim 12, wherein $R_2$ is formyl or acetyl.

16. A method according to claim 12, wherein $R_3$ is H, $C_{1-6}$alkyl or fluoride.

17. A method according to claim 12, wherein said chiral acid is (1R)-(−)-10-camphorsulfonic acid.

18. A method according to claim 12, wherein said two diastereomeric salts comprise a first more soluble diastereomeric salt and a second less soluble diastereomeric salt.

19. A process according to claim 11, wherein said compound of formula IV is optically active cis-2-hydroxymethyl-4-(cytosin-1'-yl)-1,3-oxathiolane.

20. A process according to claim 19, wherein said optically active cis-2-hydroxymethyl-4-(cytosin-1'-yl)-1,3-oxathiolane is crystalline.

21. A process according to claim 19, wherein said optically active cis-2-hydroxymethyl-4-(cytosin-1'-yl)-1,3-oxathiolane is (−) enantiomer.

22. A process according to claim 19, wherein said optically active cis-2-hydroxymethyl-4-(cytosin-1'-yl)-1,3-oxathiolane is (+) enantiomer.

23. A process according to claim 1, wherein said optically active cis-2-hydroxymethyl-4-(cytosin-1'-yl)-1,3-oxathiolane has an enantiomeric excess of 60% or higher.

24. A process for producing an optically active compound of formula I or formula II:

I

II wherein:
$R_1$ is H, $C_{1-6}$alkyl, $C_{6-12}$aryl, $C_{6-12}$arylalkyl, $(CO)C_{1-6}$alkyl, $(CO)O—C_{1-6}$alkyl, $(CO)C_{6-12}$aryl, or $(CO)C_{6-12}$arylalkyl;
$R_2$ is H, $C_{1-6}$alkyl or CO—$R_5$;
$R_3$ is H, $C_{1-6}$alkyl, bromide, chloride, fluoride, iodide or $CF_3$; and
$R_5$ is H or $C_{1-6}$alkyl;
said process comprising:
a) reacting a compound of formula III in the cis configuration:

III with a chiral acid and an achiral acid to produce a mixture of two diastereomeric salts and an enantiomeric salt, wherein said chiral acid is (1R)-(−)-10-camphorsulfonic acid, (−)-2,3-dibenzoyl-L-tartaric acid, (+)-L-tartaric acid or (−)-L-malic acid;
b) recovering a mixture of said two diastereomeric salts containing an excess of one of said two diastereomeric salts;
c) converting said one of said two diastereomeric salts into said optically active compound of formula I or formula II.

25. A method according to claim 1, wherein
said compound of formula III is (+/−)-cis-2-hydroxymethyl-4-(cytosin-1'-yl)-1,3-oxathiolane,
in a) a racemic mixture of (+/−)-cis-2-hydroxymethyl-4-(cytosin-1'-yl)-1,3-oxathiolane is dissolved in a solvent and heated in the presence of a chiral acid and an achiral acid to form a solution comprising the two following diastereoisomeric salts:
(−)-cis-2-hydroxymethyl-4-(cytosin-1'-yl)-1,3-oxathiolane•chiral salt, and
(+)-cis-2-hydroxymethyl-4-(cytosin-1'-yl)-1,3-oxathiolane•chiral salt;
in b) the solution is cooled to promote crystallization of said diastereoisomeric salts, and recovering the resultant crystals, said crystals comprising an optically active mixture of said two diastereoisomeric salts, and
in c) said optically active mixture of said two diastereoisomeric salts is treated to remove the (1R)-(—)-10-camphorsulfonic acid so as to obtain an optically active mixture of cis-2-hydroxymethyl-4-(cytosin-1'-yl)-1,3-oxathiolane.

26. The method according to claim 25, wherein said achiral acid is hydrochloric acid.

27. The method according to claim 1, wherein the solvent is an aqueous/organic solvent mixture.

28. The method according to claim 27, wherein the organic solvent is methanol or isopropanol.

29. The method according to claim 27, wherein the solvent is a mixture of 95% of water and 5% of methanol.

30. The method according to claim 27, wherein the solvent is a mixture of 50% of water and 50% of isopropanol.

31. The method according to claim 1, wherein in a), the mixture is heated at a temperature between room temperature and 70° C.

32. The method according to claim 1, wherein in b), the mixture is cooled at a temperature between room temperature and -10° C.

33. The method according to claim 1, wherein c) is performed by circulating said optically active mixture of said two diastereoisomeric salts through an ion exchange column.

34. A method according to claim 12, wherein
said compound of formula III is (+/−)-cis-2-hydroxymethyl-4-(cytosin-1'-yl)-1,3-oxathiolane,
in a) a racemic mixture of (+/−)-cis-2-hydroxymethyl-4-(cytosin-1'-yl)-1,3-oxathiolane is dissolved in a solvent and heated in the presence of a chiral acid and an achiral acid to form a solution comprising the two following diastereoisomeric salts:
(−)-cis-2-hydroxymethyl-4-(cytosin-1'-yl)-1,3-oxathiolane•chiral salt, and
(+)-cis-2-hydroxymethyl-4-(cytosin-1'-yl)-1,3-oxathiolane•chiral salt;
in b) the solution is cooled to promote crystallization of said diastereoisomeric salts, and recovering the resultant crystals, said crystals comprising an optically active mixture of said two diastereoisomeric salts, and
in c) said optically active mixture of said two diastereoisomeric salts is treated to remove the (1R)-(−)-10-camphorsulfonic acid so as to obtain an optically active mixture of cis-2-hydroxymethyl-4-(cytosin-1'-yl)- 1,3-oxathiolane.

35. The method according to claim 34, wherein said optically active mixture of said two diastereoisomeric salts comprises an excess of (−)-cis-2-hydroxymethyl-4-(cytosin-1'- yl)-1,3-oxathiolane•(1R)-(−)-10-camphor-sulfonate over (+)-cis-2-hydroxymethyl-4-(cytosin-1'-yl)-1,3-oxathiolane•(1R)-(−)-10-camphorsulfonate salt.

36. The method according to claim 34, wherein said optically active mixture of cis-2-hydroxymethyl-4-(cytosin-1'-yl)-1,3-oxathiolane has an enantiomeric excess higher than 60%.

37. The method according to claim 34, wherein said achiral acid is hydrochloric acid.

38. The method according to claim 34, wherein the solvent is an aqueous/organic solvent mixture.

39. The method according to claim 38, wherein the organic solvent is methanol or isopropanol.

40. The method according to claim 38, wherein the solvent is a mixture of 95% of water and 5% of methanol.

41. The method according to claim 38, wherein the solvent is a mixture of 50% of water and 50% of isopropanol.

42. The method according to claim 34, wherein in a), the mixture is heated at a temperature between room temperature and 70° C.

43. The method according to claim 34, wherein in b), the mixture is cooled at a temperature between room temperature and −10° C.

44. The method according to claim 34, wherein c) is performed by circulating said optically active mixture of said two diastereoisomeric salts through an ion exchange column.

* * * * *